(12) United States Patent
Kucklick

(10) Patent No.: US 11,185,402 B2
(45) Date of Patent: Nov. 30, 2021

(54) METHOD AND DEVICES FOR IMPLANTATION OF BIOLOGIC CONSTRUCTS

(71) Applicant: Smith & Nephew, Inc., Memphis, TN (US)

(72) Inventor: Theodore R. Kucklick, Campbell, CA (US)

(73) Assignee: Smith & Nephew, Inc., Memphis, TN (US)

( * ) Notice: Subject to any disclaimer, the term of this patent is extended or adjusted under 35 U.S.C. 154(b) by 281 days.

(21) Appl. No.: 16/404,619

(22) Filed: May 6, 2019

(65) Prior Publication Data

US 2019/0254802 A1    Aug. 22, 2019

Related U.S. Application Data

(63) Continuation of application No. 15/157,117, filed on May 17, 2016, now Pat. No. 10,278,801, which is a continuation-in-part of application No. 14/084,521, filed on Nov. 19, 2013, now Pat. No. 9,878,141, which is a continuation-in-part of application No. 13/088,327, filed on Apr. 15, 2011, now Pat. No. 8,585,773.

(60) Provisional application No. 61/324,746, filed on Apr. 15, 2010.

(51) Int. Cl.
| | | |
|---|---|---|
| *A61F 2/00* | (2006.01) | |
| *A61B 17/34* | (2006.01) | |
| *A61B 17/04* | (2006.01) | |
| *A61M 39/06* | (2006.01) | |
| *A61B 90/57* | (2016.01) | |

(52) U.S. Cl.
CPC ........ *A61F 2/0063* (2013.01); *A61B 17/3468* (2013.01); *A61B 17/0469* (2013.01); *A61B 17/0483* (2013.01); *A61B 17/3417* (2013.01); *A61B 17/3421* (2013.01); *A61B 17/3423* (2013.01); *A61B 90/57* (2016.02); *A61F 2002/0072* (2013.01); *A61F 2210/0014* (2013.01); *A61M 39/0606* (2013.01)

(58) Field of Classification Search
CPC ........ A61B 17/12113; A61B 17/12168; A61B 2017/00867; A61B 2017/00526; A61F 2/07; A61F 2/90; A61F 2/848; A61F 2250/0048; A61F 2002/823; A61F 2220/0075

See application file for complete search history.

(56) References Cited

U.S. PATENT DOCUMENTS

| | | | |
|---|---|---|---|
| 5,383,477 | A | 1/1995 | DeMatteis |
| 5,397,331 | A | 3/1995 | Himpens |
| 5,405,360 | A | 4/1995 | Tovey |
| 6,428,546 | B1 | 8/2002 | Cancel |
| 8,585,773 | B1 | 11/2013 | Kucklick |
| 8,888,811 | B2 | 11/2014 | Levin et al. |
| 8,906,045 | B2 | 12/2014 | Levin |

(Continued)

FOREIGN PATENT DOCUMENTS

WO    WO-2009104182 A2  *  8/2009    .......... A61B 17/064

*Primary Examiner* — Julian W Woo
(74) *Attorney, Agent, or Firm* — Seager, Tufte & Wickhem LLP

(57) ABSTRACT

Systems for delivering a sheet-like implant including a means of deploying and orienting the sheet-like implant within the body.

15 Claims, 9 Drawing Sheets

(56) References Cited

U.S. PATENT DOCUMENTS 9,393,002 B2 7/2016 Iceman et al.
9,878,141 B2 1/2018 Kucklick \* cited by examiner

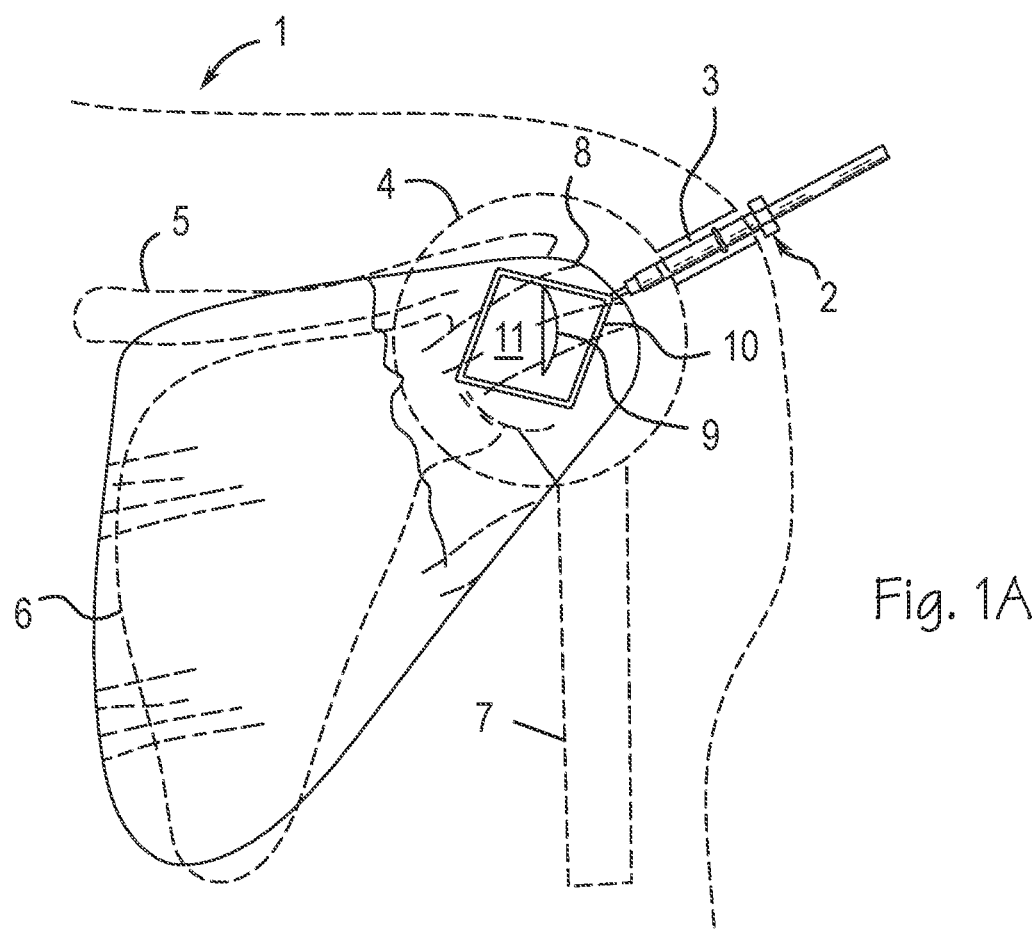
Fig. 1A
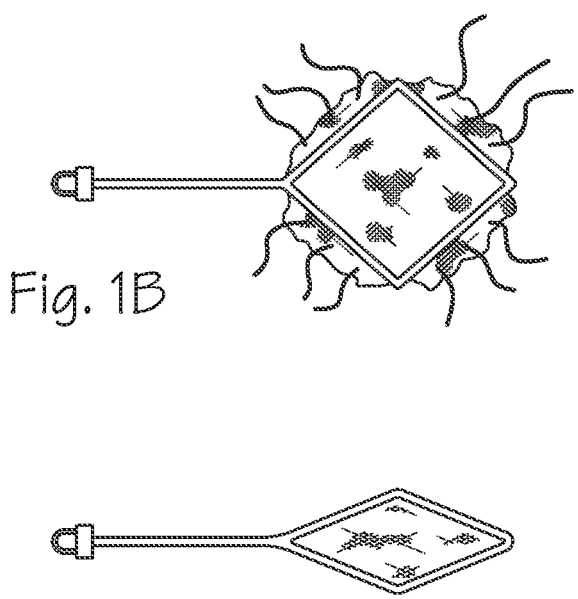
Fig. 1B
Fig. 1C
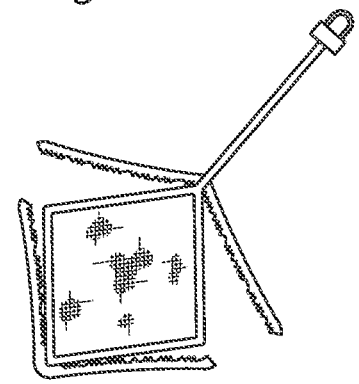
Fig. 1D

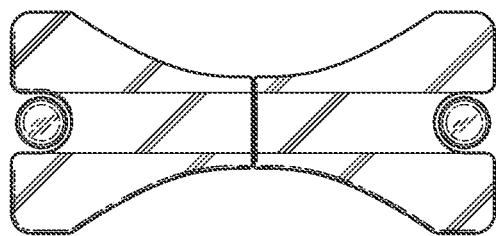
Fig. 6A
Fig. 6B
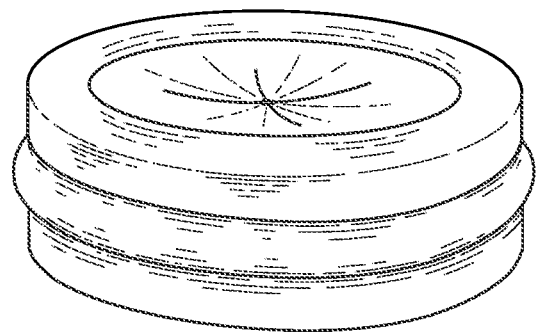
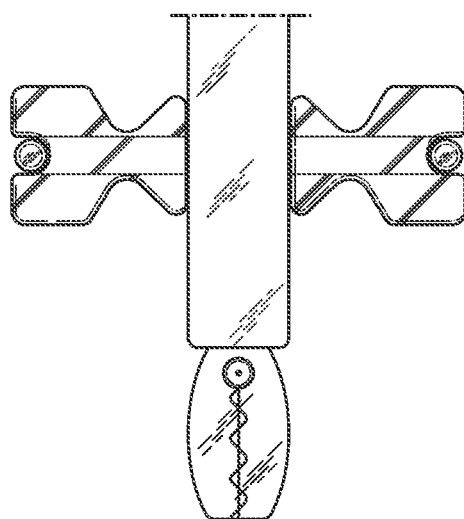
Fig. 6C

Section A-A

Section B-B

METHOD AND DEVICES FOR IMPLANTATION OF BIOLOGIC CONSTRUCTS

RELATED APPLICATIONS

This application is a continuation of application Ser. No. 15/157,117, filed May 17, 2016, now U.S. Pat. No. 10,278, 801, which is a continuation-in-part of application Ser. No. 14/084,521, filed Nov. 19, 2013, now U.S. Pat. No. 9,878, 141 which is a continuation-in-part of application Ser. No. 13/088,327, filed Apr. 15, 2011, now U.S. Pat. No. 8,585, 773, which claims priority to U.S. Provisional Patent Application 61/324,746 filed Apr. 15, 2010.

FIELD OF THE INVENTION

The inventions described below relate to the field of arthroscopic surgery and more specifically to implantation of biologic constructs.

BACKGROUND OF THE INVENTIONS

Biologic constructs, which include "regenerative tissue matrices" "acellular tissue matrices" or "collagen scaffolds" and other such substances, are small sheets or disks of flexible, engineered biomaterial, such as collagen or fibrin, decellularized dermal matrix crosslinked and sterilized xenograft tissues, and "platelet-rich-plasma" patches sometimes totally devoid of living cell material and sometimes loaded with active adjuncts such as biologic growth factors. Biologic constructs may also be tissue-engineered from mesenchymal stem cells. For the purposes of this application, the term biologic construct refers to any sheet-like or disc-like configuration of regenerative tissue matrix, acellular tissue matrices or collagen scaffolds, or similar materials suitable for placement within the body to promote healing.

Biologic constructs and implants are growing rapidly in popularity for the repair of joint pathologies. Biologic constructs may be a new alternative for carpal arthroplasty in patients with clinical conditions such as osteonecrosis. Biologic constructs are a family of biologically derived implants to promote tissue growth or to patch and repair tissue defects and tears. These include the repair of arthritic cartilage, the joining of tendons to bone and the bridging of degenerated rotator cuff in the shoulder. Biologic constructs, and graft material such as platelet rich fibrin membrane, acellular dermal allograft, (MTF) and xenograft materials (Pegasus Biologics) and graft patches (Wright Medical Graftjacket) have enabled the reconstruction and treatment of previously untreatable and irreparable musculoskeletal injuries and pathologies. Biologic constructs now occupy an increasingly important place in the orthopedic surgeons armamentarium.

One of the key problems with biologic constructs is that the delivery instrumentation has not kept pace with advances in these implants. For example, fluid seals effectively hold fluid, but do not allow passage of sutures and metal instruments through the biologic constructs without tearing and damage. This can render the construct useless, and add significantly to the cost of the case, as these implants can be fragile as well as expensive. A damaged implant can result in several hundred dollars of added expense.

In addition to these constructs being soft, floppy, and prone to damage from tearing, suture management is very difficult, both during the preparation of the implant outside the patient as well as managing the implant and sutures when the implant is manipulated and attached in the joint. Currently an implant construct is hand-held with hemostats by an assistant while the graft is prepared with sutures.

An important clinical need exists to make these biologic constructs easier to prepare, handle, deliver, and implant so that the potential of these important advances in biologics can be fully realized.

SUMMARY

The present invention solves the most important problems with biologic constructs, that is, preparation of the graft prior to insertion into the patient, the ability to pass the fragile implant into the joint space without damaging or tearing the implant, and being able to manipulate the soft and floppy implant within the joint space. All of these improvements to the delivery instrumentation will reduce costs, reduce risks to the patient, and greatly improve the speed and success of the procedure.

There are four basic components to the system: 1) having a frame to prepare the graft outside the body, 2) having a seal system that allows passage of a large, soft construct without damage, and has the ability to be fluid-tight 3) a means of deploying and orienting the construct within the body and 4) a means of managing the sutures.

There are two basic procedures being addressed: one is to bridge a massively retracted and irreparable rotator cuff tear, (with a sheet of repair material) and the other is to augment a tendon to bone repair in order to promote healing of tendon to bone (platelet rich patch).

BRIEF DESCRIPTION OF THE DRAWINGS

FIGS. 1A, 1B, 1C, and 1D illustrate the kite.
FIGS. 6A, 6B, and 6C illustrate the sphincter seal.

DETAILED DESCRIPTION OF THE INVENTIONS

Figure 2A:
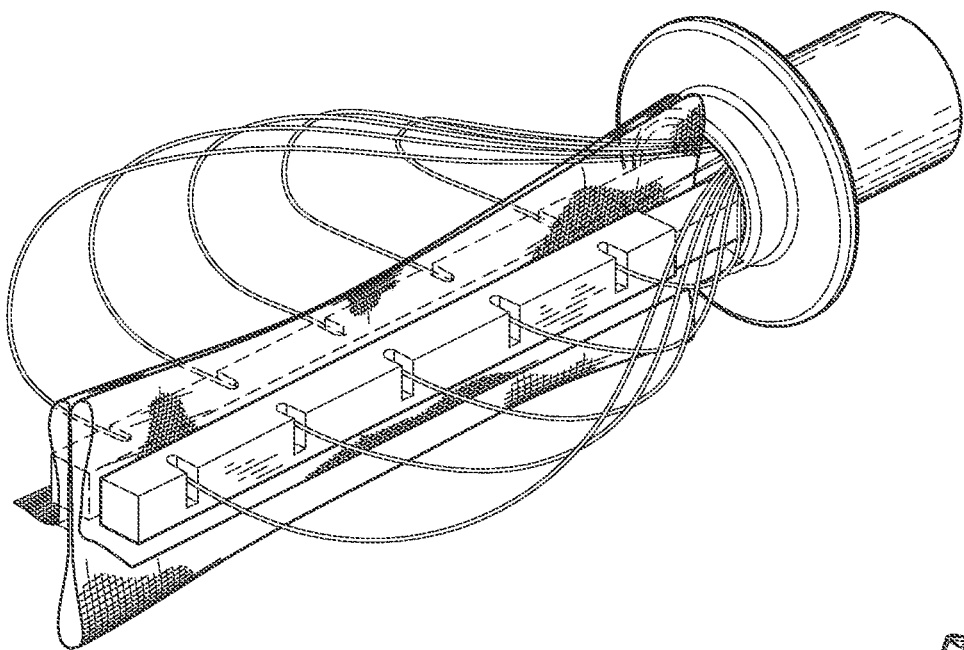
FIGS. 2A and 2B illustrate the cage.

The methods and devices described below provide for convenient prepping and delivering of a biologic construct repair for shoulder and joint surgery into an arthroscopic workspace. There are four basic components to the system: 1) a frame to prepare the graft outside the body, 2) a seal system that allows passage of a large, soft construct without damage, and has the ability to be fluid-tight 3) a means of deploying and orienting the construct within the body and 4) a means of managing the sutures.

FIGS. 1B, 1C, 1D, and 1A show a "kite" graft repair and delivery system. The "kite" is a loop of superelastic or shape memory nickel-titanium with clamps that hold the construct, and is delivered through a tube and deployed inside the body. This design calls for a nitinol or hinged frame with integrated clamps that allow the biologic construct sheet to be folded, and delivered either through a surgical wound portal, or a cannula device to a site to be repaired, such as a torn rotator cuff in a shoulder. This design allows the graft to be prepped outside the body with sutures, and held in a collapsible frame for handling, and to be deployed within a body. The frame has a feature to allow it to be releasably attached to a handle for insertion through a surgical wound or cannula.

As shown in FIG. 1A, in use, the surgeon delivers the biologic construct to a joint within the body of a patient 1 by creating an arthroscopic workspace 4 around the joint and inserting a cannula 3 through the skin of the patient proximate the arthroscopic workspace. A sheet of biologic construct 11 is provided. A collapsible first frame 10 is configured to hold the sheet of biologic construct 11. The surgeon attaches the sheet of biologic construct to the collapsible first frame, collapses the collapsible first frame with the sheet attached such that the frame and sheet fit, in a collapsed configuration, through the cannula. The surgeon inserts the collapsible first frame and sheet, in the collapsed configuration, through the cannula 3 and into the arthroscopic workspace; expanding the collapsible first frame and sheet within the workspace and positioning the sheet proximate an intended site of implantation; releasing the sheet from the collapsible first frame, collapsing the collapsible first frame and removing the collapsible first frame from the workspace; and securing the sheet to body tissue within the workspace.

The delivery device shown in FIG. 1A through 1D comprises an elongate insertion portion 2 having a proximal end and a distal end adapted for insertion into an arthroscopic workspace through a cannula or small incision proximate the workspace; a grasping member disposed on the distal end of the elongate insertion portion, wherein the grasping member comprises a collapsible frame comprising a first frame member which is collapsible from a wide configuration which tensions the sheet into a substantially flat configuration to a narrow configuration adapted for insertion into the arthroscopic workspace through the cannula or small incision proximate the workspace. The grasping member further comprise a clamping member adapted to trap the sheet between the clamping member and the first frame.

The first frame member can be rectangular, and attached to the elongate insertion portion at a corner of the frame. The first frame member can be rectangular, and attached to the elongate member at a corner of the frame, and the clamping member also comprises an articulating arm that may be selectively apposed to a side of the rectangular frame to trap the sheet between the clamping member and the frame. The first frame member can be rectangular and attached to the elongate member at a corner of the frame and be hinged at the remaining three corners of the frame. The first frame member can be rectangular comprising a superelastic material. The first frame member can also be circular or elliptical.

Figure 2B:
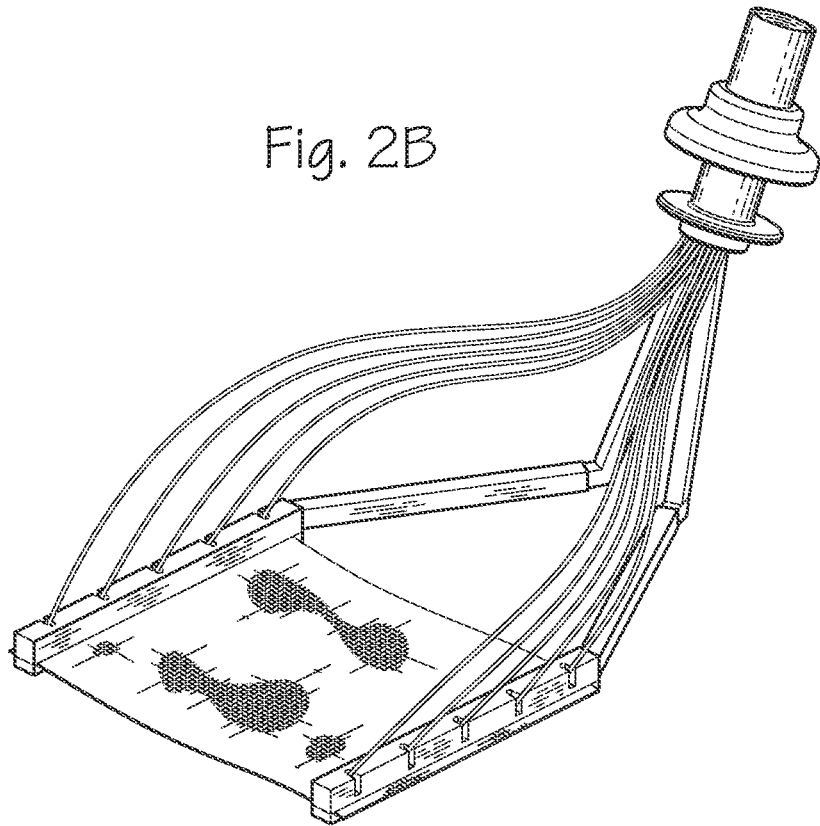

Another embodiment is where the holders for the construct are "legs" made of a preshaped spring material. This embodiment is shown in FIGS. 2A and 2B. Inserted in the tube in a closed position, the implant is folded up on the end. At the surgical site, the legs spread open inside, for example the shoulder at the surgical site. The legs spring open, which puts the implant in an open unfolded position. This device comprises an elongate insertion portion having a proximal end and a distal end adapted for insertion into an arthroscopic workspace through a cannula or small incision proximate the workspace and a pair of grasping jaws disposed on the distal end of the insertion portion. The pair of grasping jaws pivotably engaged with the elongate insertion portion such that they may be moved in away from each other to an open configuration and tension the biologic construct to a flat configuration, and closed in apposition to each other to fold the biologic construct between the pair of grasping jaws. Also, each of the pair of grasping jaws is operable to grasp the biologic construct and release the biologic construct. At least one of the grasping jaws includes a plurality of slots adapted to accept a suture segment attached to the biologic construct, as shown in FIG. 2A.

The grasping jaws can be made of a superelastic or resilient material biased to the open configuration, such that the grasping jaws may be forced in apposition to each other to fit into a cannula and thereafter superelastically or resiliently open upon exit from a distal end of the cannula.

Figure 3A:
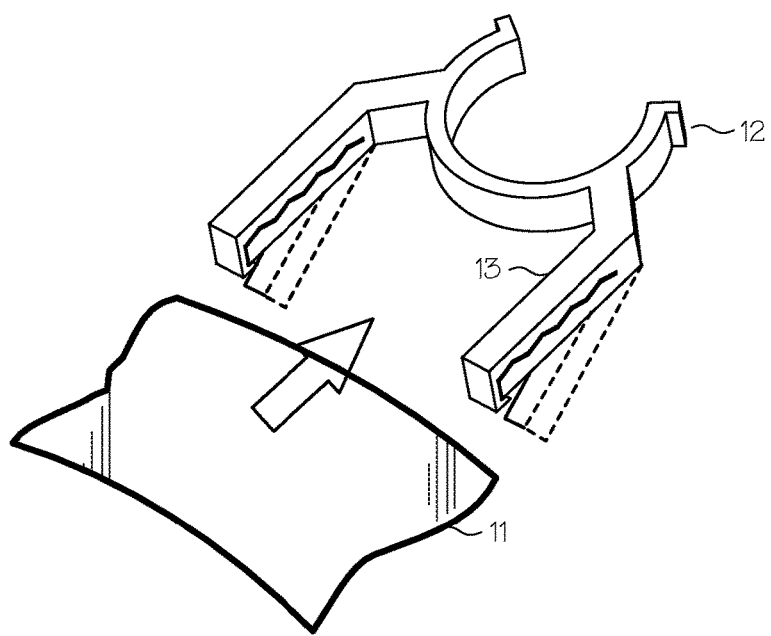
FIGS. 3A and 3B illustrate the implant frame and clamp.
Figure 3B:
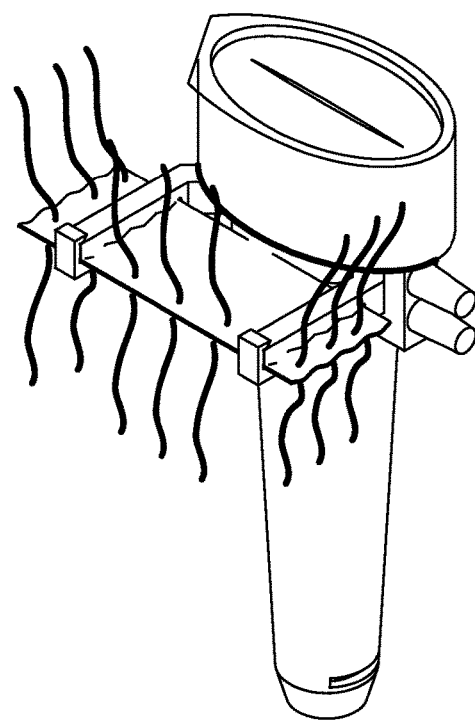

FIGS. 3A and 3B show an implant graft holder. The graft holder holds a tissue construct patch 11 in place for suturing. Currently, an assistant has to hold the patch in the air with two hemostats. Instead of requiring assistance, the present implant graft holder includes a clamp 12 and frame 13 that are detachable from the cannula for graft prep, and easily removable when the suturing procedure is complete. The implant frame holds the implant grafts for the surgeon while the surgeon places the sutures in the graft. The clamp removably clips to the cannula, as shown in FIG. 3B. The implant clamps into the frame. The frame is flexible and generally made of injection moldable plastic or other suitable material. The frame holds the implant in place for easy suture placement.

A second frame is adapted to hold the sheet to the cannula, secure the sheet to the second frame, secure a number of suture segments to the sheet while the sheet is secured to the second frame, and thereafter transfer the sheet to the collapsible first frame and perform the inserting step. The sheet can also be secured to body tissue within the workspace with the suture segments with an interrupted suture technique.

Figure 4A:
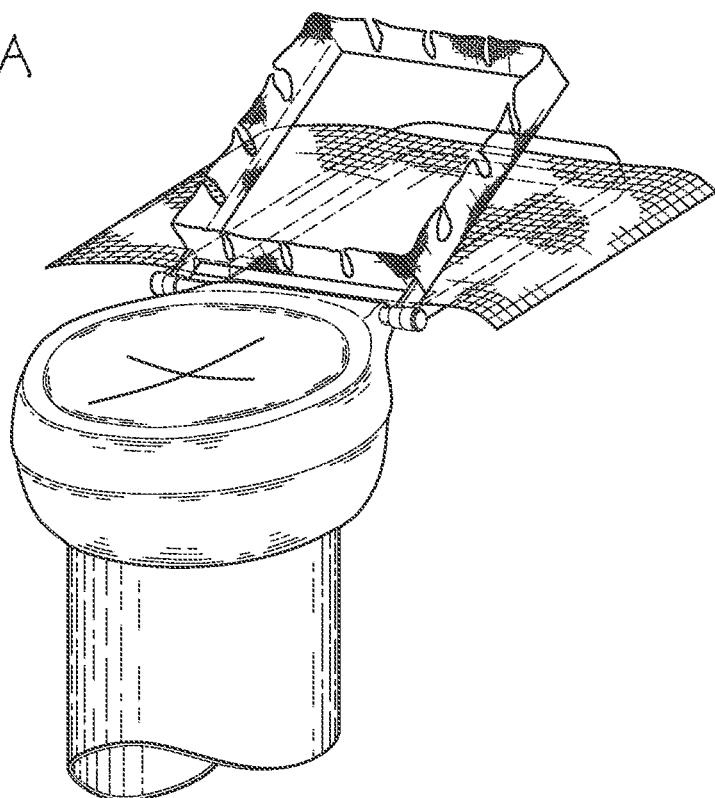
FIGS. 4A and 4B illustrate the suture management accessory.
Figure 4B:
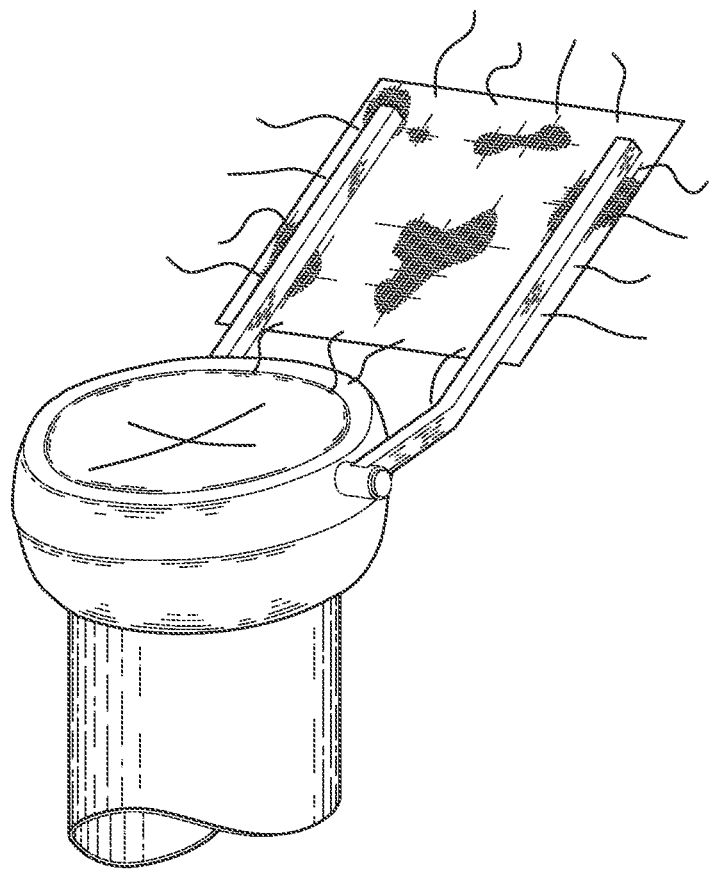

FIGS. 4A and 4B illustrate an accessory that allows a biologic construct sheet to be secured in a flat form, to be prepared with sutures for sewing into a defect, and a means for these sutures to be sorted and managed to enable efficient knot-tying and prevent tangling of the sutures as the prepared construct is delivered into the surgical space and secured into the tissue defect. Detachable allows back table prep and transfer.

Figure 5A:
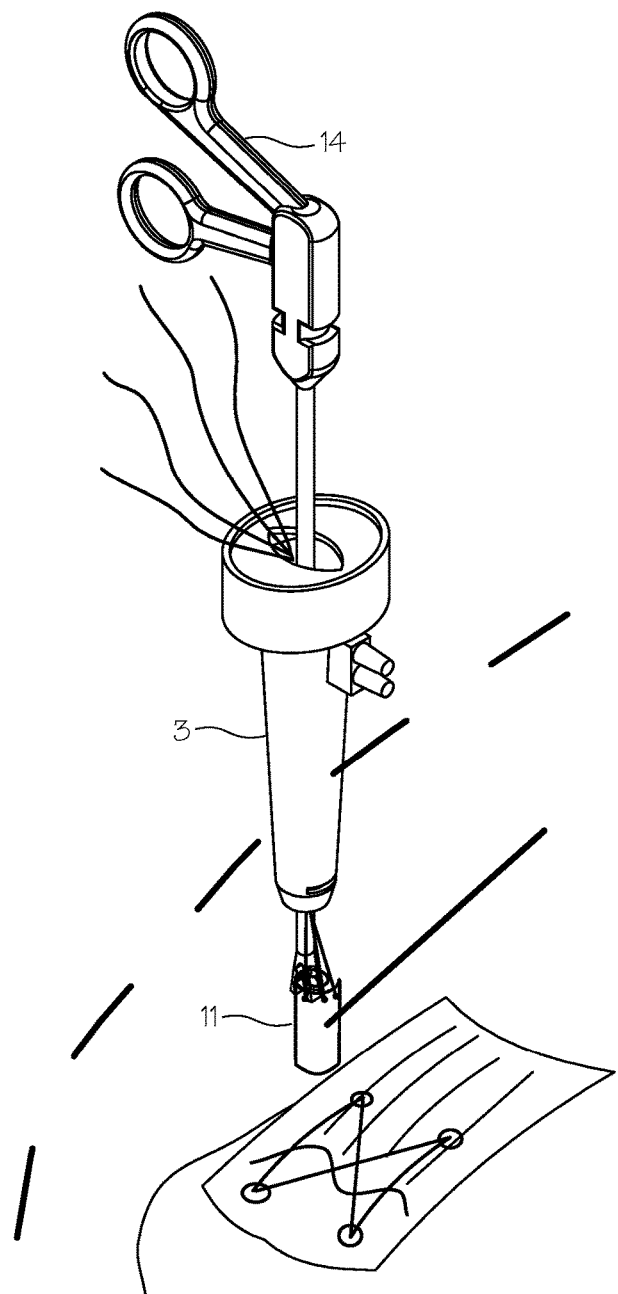
FIGS. 5A and 5B illustrate the coin purse cannula.
Figure 5B:
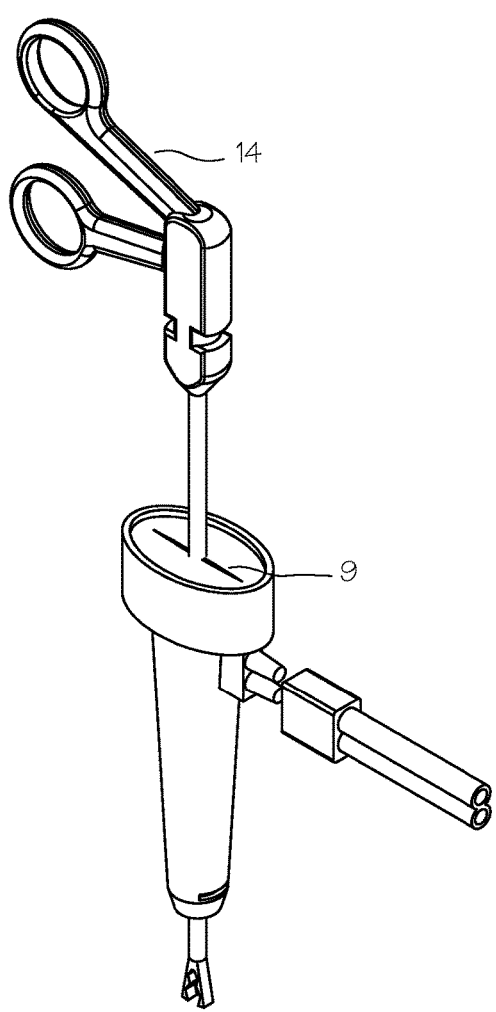

FIGS. 5A and 5B show a cannula and seal system that provides for a way to pass a larger object through a cannula. Traditional septum seals are too tight for this. The seal opening at the end of the cannula is oval in shape and made of a flexible material that when pinched, opens the slit 9. When the surgeon lets go, the slit seals back up again. This provides for a way to pass larger or fragile items like biologic graft patches and gelatinous platelet blob implants into the surgical site. As shown in FIG. 5A, the grasper 14 is inserted into the seal at the top of the cannula, with the implant 11 attached with the grasper, the grasper is inserted into the cannula 3 and the graft patch is delivered to the rotator cuff 6 at the repair site.

The "coin purse" seal shown in FIGS. 5A and 5B are part of a system that allows a large, floppy biologic construct to be prepared outside the patient, passed through a cannula, and arranged in place inside a body arthroscopically. The "coin purse" cannula is one embodiment that allows passage of a large soft object like a biologic sheet, and still allows the seal to close and prevent the leakage of fluid from the joint. The coin purse cannula seal allows for passage of larger objects into the joint, e.g. biologics and tissue implants. When the seal is closed, it creates a fluid seal and distension. The septum opens to allow passage of large implant constructs that do not fit thru conventional cannulae and allows access to endoscopic tissue repair sites, e.g. rotator cuff repair 6.

Figure 7A:
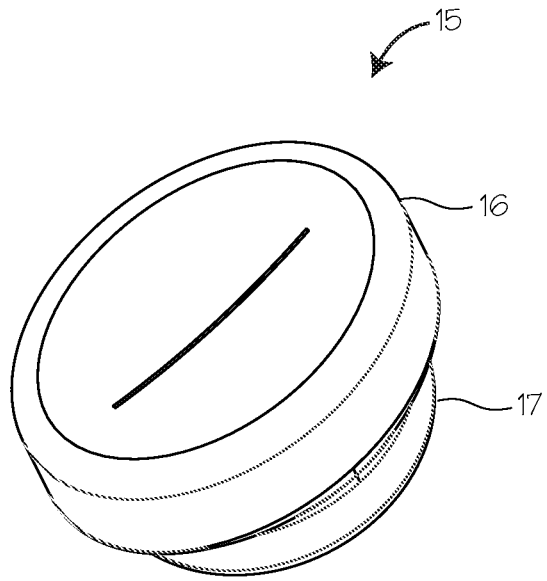
FIGS. 7A and 7B illustrate the features of the coin purse cannula illustrated in FIGS. 5A and 5B.
Figure 7B:
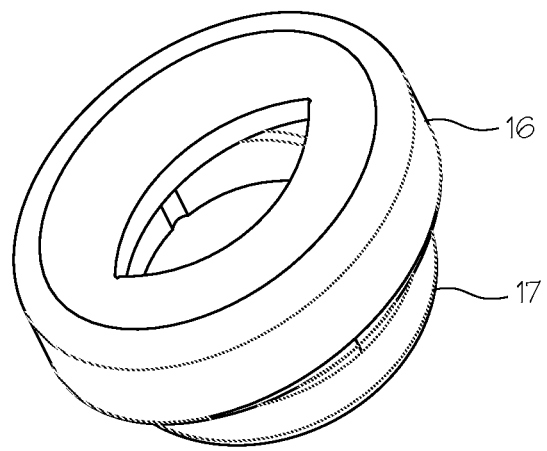

Details of the coin purse seal are illustrated in FIGS. 7A and 7B and FIGS. 8A, 8B and 8C. The seal 15 is a single unitary piece having a first section 16 with an oval or elliptical top face. The seal surface is inwardly curved as illustrated in FIG. 7A. The first section has a central inwardly curving or parabola shape that curves towards a slit on the top face. The seal also has a second section 17 integrally formed to the first section that includes a narrower diameter than the first section. The second section of the seal is shaped to allow the seal to be secured to the proximal end of a cannula. The seal is made of an elastomeric material that opens along the slit upon application of pressure, or pinching of the seal, as illustrated in FIG. 7B. The seal defaults to a closed position when the seal is no longer pinched, as illustrated in FIG. 7A. Pressure applied to the seal along the major axis of the ellipse, or perpendicular to and along the top and bottom of the slit, allows the seal to be squeezed into an open position to allow passage of instrument or biological constructs. The configuration of the seal allows the seal to act as a valve so that when in a closed position, hydrostatic pressure on the convex inner surface of the seal pushes the seal closed. The fluid pressure against the inner convex seal surface maintains the seal in a closed position. The curved surface causes the lips of the seal to open inward and allow larger objects to pass through and then close when the seal is not being pinched open. Water pressure acts on the inner curved surface to force the seal lips together and form a tighter seal as the water pressure increases. The seal may also include a circular wiper seal distal to the pinch open seal.

Figure 8A:
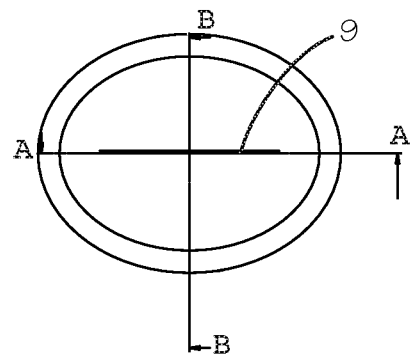
FIGS. 8A, 8B and 8C illustrate the specific features of the seal of FIGS. 7A and 7B in greater detail.
Figure 8B:
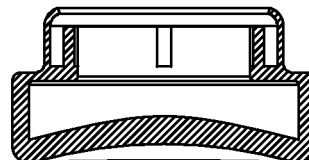
Figure 8C:
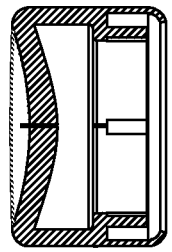

FIGS. 8A, 8B and 8C illustrate the specific features of the seal of FIGS. 7A and 7B in greater detail. FIG. 8A shows a top view of the seal having a top surface in the shape of an oval or ellipse. FIG. 8B illustrates cross section A-A of FIG. 8A along the major axis of the ellipse, also showing a central inwardly curved or parabola shape that curves towards the slit on the top face. FIG. 8C illustrates the cross section B-B of FIG. 8A along the minor axis of the ellipse, also showing the parabola surface that curves towards the slit in the central top face of the seal. Water pressure exerted on the convex surface of the parabola maintains the seal in a closed position and maintains the seal in a fluid-tight position so that no fluid passes through the seal until pressure is applied and the seal is opened by the user.

Another seal design is shown in FIGS. 6A, 6B, and 6C. This seal acts like a sphincter. The seal has a low durometer of 10-30A with a stiffer o-ring of 40-80A. The center seal stretches while the O-ring pulls the seal closed when the instrument is removed. This dual-compliance system allows easy passage of instrument and sealing of septum in "sphincter-like" manner. It is a "dual state" seal that is tight and leak resistant when the O-ring is in place, and more compliant when the O-ring is slipped out of its groove. The O-ring may be slipped back in the groove for a tighter seal once the implant is passed through. This also allows passage of large, soft implants without damaging the implant, and allows returning to a fluid-tight seal state.

Figure 9:
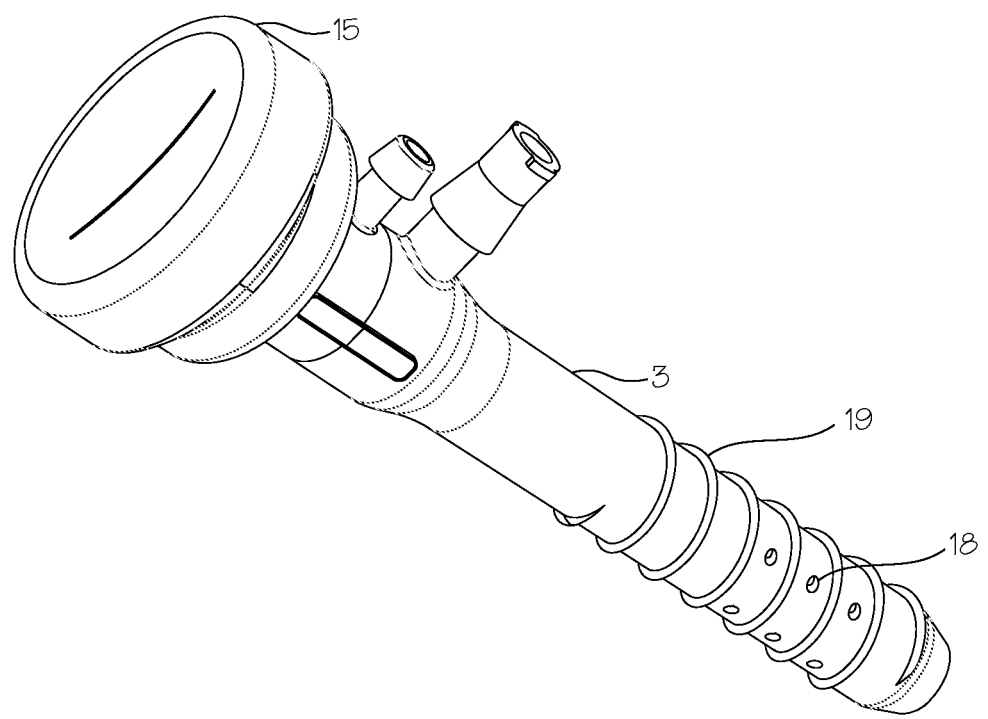
FIG. 9 illustrates a seal system that allows passage of an instrument or a large biological construct through the seal.

FIG. 9 illustrates a seal system that allows passage of an instrument or a large biological construct through the seal. The seal 15, detailed in FIGS. 7 and 8, is removably attached to a cannula 3. The cannula includes openings 18 to allow for fluid flow through the cannula and out of the openings. Windings 19 on the outside of the cannula also allow for securement of the cannula in position.

In use, the seal 15 is affixed to the proximal end of a cannula and whereupon the distal end of the cannula is delivered through a surgical wound portal to a site to be repaired such as a torn rotator cuff in a shoulder. When an arthroscopic instrument or biological construct needs to be introduced to the repair site, pressure is applied along the major axis of the seal (or perpendicular to the slit) to open the lips or slit on the top face of the seal. The applied pressure breaks the hydrostatic pressure exerted under the slit and allows access to the repair site for introduction of instruments or biologic constructs to the repair site. When access to the repair site is no longer needed, pressure is removed from the first section, the slit or lips close and remain closed under the hydrostatic pressure applied to the parabola surface of the first surface.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. An implant delivery device for delivering a sheet-like implant through a cannula, the implant delivery device comprising:
    an implant holder assembly having a distal end, a proximal end and separable first and second legs each having a proximal and distal end, with the proximal ends of the first and second legs secured to the distal end of the implant holder assembly;
    wherein the first and second legs have a closed position with the legs proximate each other, and an open position with the distal ends of each leg translated in a generally transverse direction to form an open ended implant holder assembly;
    wherein the first leg and second leg comprise a superelastic material biased to the open position, such that the legs may be forced in apposition to each other to fit into the cannula and thereafter superelastically open upon exit from the distal end of the cannula; and
    at least one slot in the distal end of the implant holder assembly sized and dimensioned to engage a portion of the sheet-like implant.

2. The implant delivery device of claim 1 further comprising:
    the sheet-like implant coupled to the implant holder assembly with a first portion of the sheet-like implant disposed within the at least one slot in the implant holder assembly.

3. The implant delivery device of claim 2 wherein the cannula encloses the implant holder assembly and the sheet-like implant with the sheet-like implant in the distalend of the cannula.

4. The implant deliver device of claim 1 further comprising:
    a tube having a proximal end and a distal end wherein the tube is sized to enclose the implant holder assembly and the sheet-like implant.

5. The implant delivery device of claim 4 further comprising:

the sheet-like implant coupled to the implant holder assembly with a first portion of the sheet-like implant disposed within the at least one slot in the implant holder assembly.

6. The implant delivery device of claim 4 wherein the tube encloses the implant holder assembly and the sheet-like implant with the sheet-like implant in the distal end of the tube.

7. The implant delivery device of claim 5 wherein the tube encloses the implant holder assembly and the sheet-like implant with the sheet-like implant in the distal end of the tube.

8. An implant delivery device comprising:
a delivery shaft having a distal end, a proximal end and a longitudinal axis;
an implant retainer having separable first and second legs each having a proximal and distal end, with the proximal ends of the first and second legs secured to the distal end of the delivery shaft;
wherein the first and second legs have a closed position with the legs proximate each other and extending parallel to the longitudinal axis of the delivery shaft, and an open position with the distal ends of each leg translated in a generally transverse direction to form an open ended implant retainer; and
a tube having a proximal end and a distal end wherein the tube is sized to enclose the delivery shaft, the implant retainer and a sheet-like implant;
wherein the first leg and second leg comprise a superelastic material biased to the open position, such that the legs may be forced in apposition to each other to fit into the tube and thereafter superelastically open upon exit from the distal end of the tube.

9. The implant delivery device of claim 8 further comprising:
a slot in the distal end of each of the first and second legs sized and dimensioned to engage a portion of the sheet-like implant.

10. The implant delivery device of claim 8 further comprising:
the sheet-like implant coupled to the implant retainer with a first portion of the sheet-like implant disposed within the slot in the first leg and a second portion of the sheet-like implant disposed within the slot in the second leg.

11. The implant delivery device of claim 10 wherein the tube encloses the delivery shaft, the implant retainer and the sheet-like implant with the sheet-like implant in the distal end of the tube.

12. An implant delivery device for delivering a sheet-like implant to an arthroscopic workspace, the implant delivery device comprising:
an implant holder having a distal end, a proximal end and a plurality of separable legs each having a proximal and distal end, with the proximal ends of the plurality of legs secured to the distal end of the implant holder;
wherein the plurality of legs have a closed position with the legs proximate each other, and an open position with the distal ends of each leg translated in a generally transverse direction to form an open ended implant holder;
wherein the plurality of legs comprise a superelastic material biased to the open position, such that the legs may be forced in apposition to each other to fit into a tube and thereafter superelastically open upon exit from the tube; and
at least one slot in the distal end of the implant holder sized and dimensioned to engage a portion of the sheet-like implant.

13. The implant delivery device of claim 12 further comprising the tube having a proximal end and a distal end wherein the tube is sized to enclose the implant holder and the sheet-like implant.

14. The implant delivery device of claim 13 further comprising:
a sheet-like implant coupled to the implant holder with a first portion of the sheet-like implant disposed within the at least one slot in the implant holder.

15. The implant delivery device of claim 14 wherein the tube encloses the implant holder and the sheet-like implant with the sheet-like implant in the distal end of the tube.

* * * * *